United States Patent

Kaufhold

Patent Number: 5,576,465
Date of Patent: Nov. 19, 1996

[54] PROCESS FOR PREPARING UNSATURATED ETHERS

[75] Inventor: Manfred Kaufhold, Marl, Germany

[73] Assignee: Huels Aktiengesellschaft, Marl, Germany

[21] Appl. No.: 460,693

[22] Filed: Jun. 2, 1995

[30] Foreign Application Priority Data

Sep. 23, 1994 [DE] Germany .......................... 44 33 949.6

[51] Int. Cl.⁶ ............................. C07C 41/28; C07C 43/16
[52] U.S. Cl. ............................................ 568/691; 568/681
[58] Field of Search ...................... 568/691, 681

[56] References Cited

U.S. PATENT DOCUMENTS 2,667,517  1/1954  Longley, Jr. .

FOREIGN PATENT DOCUMENTS 0197283  10/1986  European Pat. Off. .
3933247   1/1991  Germany .
4039950   6/1992  Germany .
9104956   4/1991  WIPO .

*Primary Examiner*—Melvyn I. Marquis
*Assistant Examiner*—D. Aylward
*Attorney, Agent, or Firm*—Oblon, Spivak, McClelland, Maier & Neustadt, P.C.

[57] ABSTRACT

A process for preparing unsaturated ethers of the formula (1)

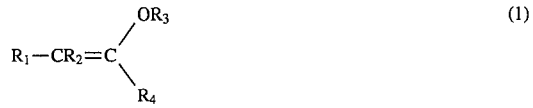

from acetals or ketal of the formula (2)

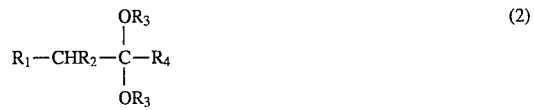

is improved by heating the acetals or ketals at from 100° to 250° C. in a high-boiling, branched carboxylic acid and obtaining the unsaturated ether as a distillate. The process, which is insensitive to contaminants, gives the unsaturated ether in high yields.

10 Claims, No Drawings

PROCESS FOR PREPARING UNSATURATED ETHERS

BACKGROUND OF THE INVENTION

1. Field of the Invention

The invention relates to a new process for preparing unsaturated ethers of the formula 1 from acetals or ketals of the formula 2 according to the following reaction scheme:

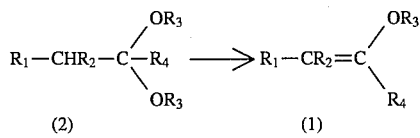

where $R_1$ is H or alkyl having from 1 to 8 carbon atoms, $R_2$ is H, $CH_3$, $CH_2H_5$ or Cl, $R_3$ is alkyl having from 1 to 8 carbon atoms and $R_4$ is H, $CH_3$, $C_2H_5$ or $C_3H_7$.

$R_1$ and $R_4$ may also be linked to one another to form a 5-membered to 7-membered ring.

The unsaturated ethers are important starting compounds for preparing pharmaceutical products and fragrances.

2. Discussion of the Background

The preparation of unsaturated ethers from acetals or ketals is known in the literature. Thus, U.S. Pat. No. 2,667,517 describes a process which uses a hydrocarbon or chlorine-containing hydrocarbon solvent and uses an aromatic or alkylaromatic sulfonic acid catalyst. In this process the solvent is strongly contaminated by high-boiling compounds which form and, therefore, EP-A-0 197 283 proposes in a similar process, a mineral oil as solvent which is burnt after use.

The process of DE-A-40 39 950 is carried out without solvents at from 160° to 200° C. using a catalyst which consists of an acid and an amine. It is well suited only for certain acetals, those of propionaldehyde, butyraldehyde and valeraldehyde. In this process too, the catalyst is contaminated by high boiling compounds which form. Low-boiling acetals such as, for example, the methyl and ethyl acetals of acetaldehyde or acetone cannot, owing to the high reaction temperatures, be reacted at atmospheric pressure by this process.

SUMMARY OF THE INVENTION

It is, therefore, an object of the present invention to provide a simple process which can be carried out in a conventional stirred apparatus at atmospheric pressure, in which the consumption of catalyst is low, in which only few high-boiling waste products are formed and which is suitable for the dissociation of a wide variety of acetals and ketals.

This object is achieved according to the invention by carrying out the reaction in a high-boiling, branched carboxylic acid at from 100° to 250° C. and obtaining the unsaturated ether as distillate.

DETAILED DESCRIPTION OF THE PREFERRED EMBODIMENTS

Suitable acetals of the formula (2) (for $R_4$=H) are primarily open-chain compounds which preferably have two identical acetal radicals $R_3$. Examples of such acetals are dimethyl acetals, diethyl acetals, di-n-propyl acetals, di-n-butyl acetals, di-i-butyl acetals, di-n-pentyl acetals, di-i-pentyl acetals, di-n-hexyl acetals and di-i-hexyl acetals of aldehydes of the general formula $R_1$—$CHR_2$—CHO, where $R_1$ and $R_2$ are as defined above.

Examples of such acetals are: acetaldehyde dimethyl acetal, acetaldehyde diethyl acetal, acetaldehyde dipropyl acetal, propionaldehyde dimethyl acetal, propionaldehyde diethyl acetal, propionaldehyde dipropyl acetal, propionaldehyde dibutyl acetal, butyraldehyde dimethyl acetal, butyraldehyde diethyl acetal, butyraldehyde dipropyl acetal, butyraldehyde dibutyl acetal, butyraldehyde dipentyl acetal, valeraldehyde dimethyl acetal, valeraldehyde diethyl acetal, valeraldehyde dipropyl acetal, valeraldehyde dibutyl acetal, valeraldehyde dipentyl acetal, isovaleraldehyde dimethyl acetal, isovaleraldehyde diethyl acetal, isovaleraldehyde dipropyl acetal, isovaleraldehyde dibutyl acetal, isovaleraldehyde dipentyl acetal, hexanal dimethyl acetal, hexanal diethyl acetal, hexanal dipropyl acetal, hexanal dibutyl acetal, hexanal dipentyl acetal, hexanal dihexyl acetal, 2-ethylhexanal dimethyl acetal, 2-ethylhexanal diethyl acetal, 2-ethylhexanal dipropyl acetal, 2-ethylhexanal dibutyl acetal, 2-ethylhexanal dipentyl acetal, 2-ethylhexanal dipentyl acetal, 2-ethylhexanal dihexyl acetal and nonanal dimethyl acetal.

Examples which may be mentioned of acetals having a chlorine as substituent are chloracetaldehyde acetals.

Suitable ketals of the formula (2) (with $R_4 \neq H$) are, for example: dimethyl, diethyl, di-n-propyl, di-n-butyl, di-i-butyl ketals of acetone, 2-butanone, 2-pentanone, 3-pentanone, 2-hexanone, 3-hexanone, cyclopentanone or cyclohexanone. The ketals can also contain alkyl substituents or even chlorine substituents (preferably 1–4 substituents).

The acids used for the reaction generally have boiling points of above 120° C. They should not distil off with the ether during the reaction, although they can boil under reflux under the reaction conditions. Preference is given to using carboxylic acids having boiling points of from 140° to 400° C., in particular having boiling points of from 250° to 400° C. The high-boiling, branched carboxylic acids usually have from 5 to 20 carbon atoms. Preference is given to using 2,2-disubstituted $C_7$–$C_{18}$-carboxylic acids. These acids contain 2 substituents in the α-position to the carboxyl group. Such neoacids are, for example, obtained in the Koch synthesis. Representatives of these acids are pivalic acid, neooctanoic, neononanoic, neodecanoic, neododecanoic and also 2,2,5-trimethyldecanoic acid. For economic reasons, the acids selected are often commercial product mixtures, thus, for example, so called neoacids having 9 or more carbon atoms, which are liquid at room temperature and can be readily handled industrially.

It is a particular advantage of the process of the invention that it can be carried out without catalysts such as, for example, sulfuric acid, p-toluenesulfonic acid and other alkylbenzenesulfonic acids or phosphoric acid. It is preferably carried out without these catalysts, although they could also be used in addition in conventional amounts.

It is very surprising that these carboxylic acids possess catalytic effects, since they are weak acids and according to the prior art strong acids are used as catalysts. Surprisingly, one obtains virtually no high-boiling byproducts which would contaminate the bottom product and necessitate a workup. Rather, the high-boiling, branched carboxylic acids can be repeatedly recycled into the reaction, which is a great economic advantage.

Furthermore, the process is very insensitive to contaminants. The acetals and ketals can thus contain small amounts of bases which are used for purification and removal of peroxides, without the activity of the medium being thereby reduced.

The process is preferably carried out continuously, long running times are achieved here without replacing the medium, although, for example, sodium hydroxide gets into the reactor with the starting materials and neutralizes part of the carboxylic acid. It is a further advantage of the process that the sodium salts thus formed do not precipitate, but remain dissolved in the acid. The salts of the carboxylic acids can be very simply reconverted into the free carboxylic acids by washing with dilute aqueous mineral acid.

In the process of the invention, no further solvent is normally required. In particular cases, if it is desirable in view of the starting material, it is also possible to add customary solvents which are stable under the reaction conditions, such as, for example, paraffins, alkylaromatics, or chlorinated hydrocarbons such as 1-chloroalkanes.

It is a great advantage of this process that it requires no special reactor, but can be carried out in any stirred apparatus fitted with a distillation column.

The process of the invention can finally also be used to prepare unsaturated ethers in which the alkoxy group is subsequently exchanged by means of an alcohol according to the following reaction.

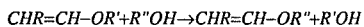
$CHR=CH-OR'+R''OH \rightarrow CHR=CH-OR''+R'OH$

To carry out the process of the invention, the high boiling, branched carboxylic acids are initially charged, heated to from 100° to 250° C., preferably to from 120° to 220° C., and the acetal or ketal is metered in continuously while a mixture, consisting of unsaturated ether, alcohol which has been eliminated and unreacted acetal or ketal, simultaneously distills over. This distillate is optionally fractionally distilled after prior washing to remove any water-soluble alcohol. If azeotropes of the ether with the alcohol occur, the alcohol is removed, for example, by means of washing with water.

The reaction is usually carried out at atmospheric pressure or slightly elevated pressure, but it is also possible to carry it out under reduced pressure.

Other features of the invention will become apparent in the course of the following descriptions of exemplary embodiments which are given for illustration of the invention, but are not intended to be limiting thereof.

EXAMPLES

EXAMPLE 1

2-Methoxypropene (MPP)

A glass apparatus was used having a five-neck flask fitted with a thermometer, stirrer and dropping funnel, whose outlet tube reached to the lowest point of the flask, and with a distillation apparatus fitted on top. The five-neck flask was charged with 250 g of neononanoic acid and the distillation receiver was charged with 1 g of potassium carbonate. 340 g (3.21 mol) of 2,(2)-dimethoxypropane (DMP), 98.2% pure, were then added continuously at 130° C. to the neononanoic acid.

The ratio of reflux to offtake was set to 2:1 on the distillation apparatus. After 4 hours, the reaction was complete, and 340 g of distillate were obtained. The bottom product gained 1 g which was colored only pale yellow.

The distillate had the following composition:

| | |
|---|---|
| MPP | 48.7 wt % |
| Acetone | 1.2 wt % |
| DMP | 22.4 wt % |
| Methanol | 27.7 wt % |

The conversion of DMP was 78% and the yield of MPP, based on conversion, was 91 wt %.

For the workup, the MPP was distilled off and washed twice with water to free the distillate of methanol. This gave a purity of 99.3%.

For recovery of the DMP, n-pentane was added to the MPP-free distillation residue and a n-pantene-methanol azeotrope was distilled off. Water was continuously added to the distillate obtained, so as to achieve a good separation of the n-pentane phase and the water-methanol phase.

The water-methanol phase obtained was separated off and discarded. The pentane was then distilled off and finally the DMP was distilled to give a pure product.

EXAMPLE 2

2-Methoxypropene (MPP)

The bottom product obtained in Example 1 was used in a total of 13 further experiments as described in Example 1. The increase in amount of bottom product was here only 14 g. The catalytic action of the bottom product showed no loss in activity. The product was liquid and readily mobile. Only a small amount of high boiling compounds formed.

EXAMPLE 3

Ethyl Vinyl Ether

The apparatus described in Example 1 was used and the procedure was similar.

The flask was charged with 260 g of neononanoic acid and the distillation receiver was charged with 3 g of sodium hydroxide solution (50% strength) for stabilization. 340 g of acetaldehyde diethyl acetal were then added continuously.

The reaction temperature was 200° C., the temperature at the top of the column was from 68° to 71° C. The distillate obtained (324 g) was distilled at atmospheric pressure. The first fraction (159 g) contained ethyl vinyl ether in a purity of 96.8% and 2.5% of ethanol. The second fraction (150 g) had the following composition:

| | |
|---|---|
| Ethyl vinyl ether | 1.6 wt % |
| Acetaldehyde diethyl acetal | 23.8 wt % |
| Ethanol | 72.3 wt % |

The conversion in this reaction was 89% and the yield, based on acetal reacted, was 86 wt %.

Washing with water gave the ethyl vinyl ether in a purity of 99.5%.

In this experiment, the bottom product gained about 1 g and was used again in the next experiment.

Comparative Example A

The procedure was as in Example 1. However, in place of neononanoic acid, 300 g of dibenzyltoluene (MARLO-THERM®, Huels AG, D-45764 Marl, Germany) and 3 g of alkylbenzenesulfonic acid (MARLON® AS 3-Saeure, Huels AG) were placed in the flask. At a reaction temperature of 200° C., 300 g of acetaldehyde diethyl acetal (98.5% pure) were metered in.

After the reaction was complete, the amount of bottom product was 321 g and after use three times was 331 g. The increase was thus 10% after the material had been used only-three times. The conversion of acetal was 57% and the yield, based on acetal reacted, was 76 wt %.

EXAMPLE 4 n-Butyl Vinyl Ether

The apparatus described in Example 1 was used and the process was as described therein, except that acetaldehyde di-n-butyl acetal was used in place of DMP and the temperature was increased to 210° C. 250 g of neononanoic acid were placed in the flask and 340 g of acetaldehyde di-n-butyl acetal were added.

A conversion of 83% and a yield of n-butyl vinyl ether, based on acetal reacted, of 70 wt % were achieved.

EXAMPLE 5

Ethyl 1-propenyl Ether

The procedure was as in Example 1; however, propionaldehyde diethyl acetal was used in place of DMP.

270 g of neononanoic acid were placed in the flask. At a reaction temperature of 200° C., 412 g of propionaldehyde diethyl acetal (97% pure) were then added. Ethyl 1-propenyl ether was obtained in a yield of 97 wt %.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing an unsaturated ether of formula (1)

$$R_1-CR_2=C\begin{cases}OR_3\\R_4\end{cases} \quad (1)$$

from an acetal or ketal of the formula (2)

$$R_1-CHR_2-\underset{\underset{OR_3}{|}}{\overset{\overset{OR_3}{|}}{C}}-R_4 \quad (2)$$

where $R_1$ is H or $C_{1-8}$ alkyl, $R_2$ is H, $CH_3$, $C_2H_5$ or Cl, $R_3$ is $C_{1-8}$ alkyl, $R_4$ is H, $CH_3$, $C_2H_3$ or $C_3H_7$, or $R_1$ and $R_4$, are bonded together to form a 5-membered to 7-membered ring, comprising the steps of heating said acetal or ketal at 100°–250° C. in a branched carboxylic acid to form a mixture containing said unsaturated ether, wherein said carboxylic acid has a boiling point of 250°–400° C.

2. The process of claim 1, wherein said carboxylic acid is a $C_{5-20}$ carboxylic acid.

3. The process of claim 1, wherein said carboxylic acid is a 2,2-disubstituted $C_7$–$C_{18}$-carboxylic acid.

4. The process of claim 1, wherein said carboxylic acid is selected from the group consisting of, neooctanoic, neononanoic, neodecanoic, neododecanoic, 2,2,5-trimethyldecanoic acids and mixtures thereof.

5. The process of claim 1, wherein said heating is from 220°–220° C.

6. The process of claim 1, wherein said acetal or ketal is an acetal selected from the group consisting of dimethyl acetals, diethyl acetals, di-n-propyl acetals, di-n-butyl acetals, di-i-butyl acetals, di-n-pentyl acetals, di-i-pentyl acetals, di-n-hexyl acetals and di-i-hexyl acetals of aldehydes of the formula $R_1$—$CHR_2$—CHO, where $R_1$ and $R_2$ are as defined above.

7. The process of claim 1, wherein said acetal is a chloroacetaldehyde acetal.

8. The process of claim 1, wherein said acetal or ketal is a ketal selected from the group consisting of dimethyl, diethyl, di-n-propyl, di-n-butyl and di-i-butyl ketals of a ketone selected from the group consisting of acetone, 2-butanone, 2-pentanone, 3-pentanone, 2-hexanone, 3-hexanone, cyclopentanone and cyclohexanone and said ketones having an alkyl or chlorine substituent.

9. The process of claim 1, wherein said heating is in the presence of a catalyst.

10. The process of claim 1, wherein said process is a continuous process.

* * * * *